(12) United States Patent
Kochergin

(10) Patent No.: US 7,265,845 B2
(45) Date of Patent: Sep. 4, 2007

(54) SURFACE CORRUGATION ENHANCED MAGNETO-OPTICAL INDICATOR FILM

(75) Inventor: Vladimir Kochergin, Westerville, OH (US)

(73) Assignee: Lake Shore Cryotronics, Inc., Westerville, OH (US)

(*) Notice: Subject to any disclaimer, the term of this patent is extended or adjusted under 35 U.S.C. 154(b) by 389 days.

(21) Appl. No.: 10/764,496

(22) Filed: Jan. 27, 2004

(65) Prior Publication Data
US 2004/0239936 A1 Dec. 2, 2004

Related U.S. Application Data

(60) Provisional application No. 60/442,539, filed on Jan. 27, 2003.

(51) Int. Cl.
*G01N 21/55* (2006.01)
*G01R 33/02* (2006.01)

(52) U.S. Cl. .................... 356/445; 324/244.1
(58) Field of Classification Search .......... 356/445; 324/244.1
See application file for complete search history.

(56) References Cited

U.S. PATENT DOCUMENTS 4,410,227 A 10/1983 Prunella et al.
5,583,690 A 12/1996 Andrae et al.
6,934,068 B2* 8/2005 Kochergin .................. 359/280

FOREIGN PATENT DOCUMENTS

DE 4027049 3/1991
JP 3-185338 A 8/1991

OTHER PUBLICATIONS

B. Ludescher, et al., "Faraday Low-temperature Microscope for observing Dynamic Magnetization processes in Superconductors" (i.e., Faraday-Tieftemperatur-Mikroskop zur Beobachtung dynamischer Magnetisierungsvorgange in Supraeitern), *Laser und Optoelektronik* 23 (1991), pp. 54-58.
L.A. Dorosinskii, et al., "Studies of HTSC crystal magnetization features using indicator magnetooptic films with in-plane anisotropy," *Physica C* 203 (1992), pp. 149-156.
M.V. Indenbom, et al., *Physica C* 166 (1990), pp. 486-496.
Safarov V.I. et al, "Magneto-optical Effects Enhanced by Surface Plasmons in Metallic Multilayer Films," *Physical Review Letters*, 73 (26), Dec. 1994. p. 3584-7.

(Continued)

*Primary Examiner*—Richard A. Rosenberger
(74) *Attorney, Agent, or Firm*—Nixon & Vanderhye PC

(57) ABSTRACT

A method of enhancing the conversion of magnetic field intensity and spatial data to optical data utilizes surface plasmon resonance combined with corrugated optical gratings of several types. Appropriate materials and methods for producing and applying said corrugations and surface plasmon resonance-producing enhancements to Magneto-Optical Indicator Films (MOIF) are described. Methods of acquiring and interpreting magneto-optical data are also described.

23 Claims, 11 Drawing Sheets

OTHER PUBLICATIONS

Kochergin V.E. et al, "Polariton enhancement of the Faraday magentooptic effect," *JETP Letters*, 68 (5), Sep. 1998, p. 400-403.

Raether H., "On the Influence of Roughness on the Optical Properties of Surfaces: Plasma Resonance Emission an dthe Plasmon Dispersion Relation," *Thin Solid Films*, 28, (1), Jul. 1975. p. 119-124.

Wallis R.F. et al, "Theory of surface polaritons in anisotropic dielectric media with application to surface magnetoplasmons in semiconductors," *Physical Review B (Solid State)*, 9 (8), Apr. 1974. p. 32424-3237.

Nikitin P.I. et al, "Surface plasmon resonance interferometry for biological and chemical sensing," *Sensors and Actuators B* B54 (1-2), Jan. 1999 p. 43-50.

Grigorenko A.N. et al, "Phase jumps and interferometric surface plasmon resonance imaging," *Appl. Phys. Lett.*, 75 (25), Dec. 1999, p. 3917-3919.

Notcovich A.G. et al, "Surface plasmon resonance phase imaging," *Appl. Phys. Lett* 76 (13), Mar. 2000. p. 1665-1667.

Rothenhausler B. et al, Surface-plasmomicroscopy, *Nature*, 332, Apr. 1988. p. 615-617.

Kochergin V.E. et al, "Phase properties of a surface-plasmon resonance from the viewpoint of sensor applications," *Quantum Electronics*, May 1998, 28 (5), p. 444-448.

Grigorenko A.N. et al, "Dark-field surface plasmon resonance microscopy," *Optics Communications*, 174 (1-4), Jan. 2000. p. 151-155.

Chern M.Y. et al, "Red Shift of Faraday Rotation in Thin Films of Completely Bismuth-Substituted Iron Garnet $Bi_3Fe_5O_{12}$," *Japanese Journal of Applied Physics*, Part 1, 38 (12A), Dec. 1999, p. 6687).

Uhlmann D.R. et al, "New optical materials by wet chemical processing," *Journal of Non-Crystalline Solids*, 196, Mar. 1996. p. 26-36.

Mansuripur, M., "The Faraday Effect," *Optics & Photonics News* (Nov. 1999).

Holm, William, Thesis, Superconducting fluctuations as a tool to probe microscopic properties of $YBa_2Cu_3O_{7-\delta}$, Stockholm, Sweden (Feb. 1996).

"Magneto-Optical Effects, The Interaction of Electromagnetic Radiation with Magnetic Media," http://www.qub.ac.uk/mp/con/magnetics_group/magnetoptics.html (last revised Jan. 4, 1998).

Densysenkov, v., "Magnetic Properties of Bismuth Iron Garnet Films," The course #5A1710/5A171 "Experimental Material Physics".

* cited by examiner

SURFACE CORRUGATION ENHANCED MAGNETO-OPTICAL INDICATOR FILM

CROSS-REFERENCES TO RELATED APPLICATIONS

This application claims the benefit of provisional application No. 60/442,539 filed Jan. 27, 2003, incorporated herein by reference.

STATEMENT REGARDING FEDERALLY SPONSORED RESEARCH OR DEVELOPMENT

Not applicable.

FIELD

The technology herein relates to a magneto-optical indicator film (MOIF), and more particularly to such films used to examine specimens with associated magnetic fields by means of a light beam reflected from said MOIF. In an illustrative exemplary non-limiting implementation, the MOIF is arranged between a specimen and a light source and the influence of the specimen's magnetic field on the MOIF is measured by means of the optical reflections from the MOIF, including the intensity, polarization and/or phase of the light.

BACKGROUND AND SUMMARY

Michael Faraday discovered magneto-optical ("MO") effects in 1845. Faraday noticed that magnetic lines of force from a magnet would affect polarized light rays passing through a glass rod. A Scottish scientist named John Kerr later published what came to be known as the Kerr electro-optic effect in 1875. This effect, for which Faraday had searched in vain some 40 years before, is the rotation of the plane of polarization of light in passing through an optical medium across which an electric potential is applied. Kerr's first results were for solid glass; but these were followed by results using liquids in cells. In the following year he published details of another effect, the magneto-optic effect using an electromagnet. The magnetic effect showed that a rotation of the plane of polarization of light occurred upon reflection from the polished pole of a magnet.

While the magneto-optical effects observed by Faraday and Kerr in media such as glass are relatively small, these effects are much larger in magnetic media. More recently, MO effects have been used for a variety of applications including magneto-optical recording (e.g., for high density data storage devices), optical communications, magnetic domain imaging, hysteresis loop plotting, Faraday microscopes, and other applications. For example, with the aid of the MO effects, dynamic processes in, for example, superconductors and magnetic structures in magnetic storage media can be examined. Other applications include, but are not limited to, imaging of electric current values and distributions in integrated circuits, visualization of magnetization dynamics of spin valves, viewing magnetic inks in currency, non-destructive testing of structural metals and imaging in permanent magnets.

For many applications, the preferable magneto-optical media is a film known as magneto-optical indicator film ("MOIF"). See for example Andrae, U.S. Pat. No. 5,583,690; B. Ludescher, et al., "Faraday Low-temperature Microscope for observing Dynamic Magnetization processes in Superconductors (i.e., Faraday-Tieftemperatur-Mikroskop zur Beobachtung dynamischer Magnetisierungsvorgange in Supraeitern"), Laser und Optoelektronik 23 (1991), pages 54–58; L. A. Dorosinskii, et al., Physica C 203 (1992), page 149; and M. V. Indenbohm, et al., Physica C 209 (1993), page 295. A device for detecting magneto-optical anisotropy, particularly of magnetic recording media, is described in U.S. Pat. No. 4,410,227. A laser polarizing microscope for observation of magnetic domains is known from JP 3-185338 (A). A Kerr microscope for examining current paths utilizing the polar Kerr effect is known from German Patent Specification DE 4027049.

Briefly, the magneto-optical Faraday effect causes a rotation of the polarization plane of polarized light by angle $\phi$ as it passes through a magneto-optical material of thickness d according to the equation $\phi = R \cdot M(x) \cdot d$, where R represents the material constant (known as Verdet constant) of the magneto-optical material and $M(x)$ represents the magnetization component at point x and parallel to the light path. The rotation of the plane of polarization is visible by observing the light at the polarizer-analyzer intersection. The so-called Kerr microscope uses the Kerr effect, which produces rotation of polarization of light reflected from magneto-optical media.

FIG. 1 shows an example prior art MOIF arrangement used to observe and/or test the magnetic characteristics of a device under test ("DUT") 4. The MOIF arrangement includes a magneto-optically active layer 1 disposed on a substrate 2. A high reflectivity layer 3 is provided at the interface with device under test (DUT) 4. Incident light 5 passes through the substrate and the active layer 1 to strike the high reflectivity layer 3. The high reflectivity layer 3 reflects the light (6) back toward the substrate 2. The polarization state 7 of the reflected light changes with the magnetic characteristics of device under test 4 due to the Kerr or Faraday magneto-optical effect, and can be observed or measured.

In general with such MOIF implementations, the constant R is so small that the Faraday effect is observed only in special materials such as Yttrium Iron Garnet or "YIG" for example. Even materials such as YIG exhibiting the highest R and small absorption require microns of light-to-MO material interaction length to get reasonable magnetic field resolution. This relatively large spatial requirement, in turn, significantly sacrifices spatial resolution. The Kerr effect, although it provides good spatial resolution, is typically too weak to provide good magnetic resolution for weak or varying magnetic fields.

Enhancement of the MO effect in MOIF is clearly needed. Optimizing the MO layer composition could bring some improvement in MOIF, but it seems doubtful that such improvement would exceed a factor of two since much effort has been expended over several decades of work on materials for such technology as bubble memories. The enhancement of MO Kerr effects near the conditions of SPR excitation have been proposed. See for example Safarov V. I. et al, *Physical Review Letters*, 73 (26), December 1994. p. 3584–7. Although a strong increase in the MO signal can be realized, this configuration may be hard to adapt for the high spatial resolution required for many imaging and visualization applications. Specifically, the exemplary optical scheme requires a prism and nearly 45 degrees angle of incidence on the MOIF, which may be hard to accomplish in microscopy.

One of the present inventors previously proposed to enhance MO Faraday effects near the condition of surface plasmon resonance ("SPR") excitation. See Kochergin V. E. et al, *JETP Letters*, 68 (5), September 1998, p. 400. The experimental structure examined in that article provided a Bi:YIG layer with a thickness of 1.9 micrometers grown on a (111) GGG substrate by liquid phase epitaxy (LPE). A diffraction grating was inscribed on it by ion etching. An Ag layer was deposited on the top of the grating to support the surface plasmons, and was covered by an Au protective layer. The grating depth was 300 nm, which was at least 20 times deeper than it should have been for the maximum effect, so the grating period was unsuitable for normal incidence operation. The end result enhanced the polarization rotation by 6 times over the polarization rotation of un-patterned YIG.

The polarization rotation of the exemplary prior art structure of Kochergin et al as a function of an angle of incidence is given in FIG. 3, which shows experimentally measured enhancement of the MO effect near the conditions of SP excitation. Although the scheme proposed in Kochergin et al has some of the same disadvantages as the Safarov et al proposal, it can be adapted for microscopy applications by choosing the correct grating period. The Kochergin enhancement coefficient was of the same order of magnitude as in Safarov et al, but the absolute value of the observed MO effect was higher by orders of magnitude. However, the Kochergin arrangement relied on a diffraction grating etched into the YIG layer. The diffraction grating structure can induce considerable demagnetization effect and increase coercive force. Therefore, that arrangement is not suitable for certain applications. Accordingly, further improvements and developments are desirable.

Exemplary illustrative arrangements disclosed herein provide an improved MOIF structure with increased magnetic field resolution, spatial resolution and visualization contrast.

One exemplary non-limiting MOIF structure is constructed in the form of multilayer stack containing at least one layer of MO-active material and at least one additional layer whose thickness and/or refractive index is modulated in a predetermined fashion and is not required to be magnetic. The modulation can be made in the form of surface or interface periodical corrugations for example. The corrugations can for example be a one-dimensional diffraction grating, the amplitude and period of which are chosen to maximize the figure of merit of the MOIF structure.

According to a further non-limiting exemplary arrangement, the corrugation can be made in a form of a two-dimensional diffraction grating the period and amplitude of modulation of which are chosen according to the desired performance of the MOIF structure. The corrugation can also be provided by a plurality of superimposed diffraction gratings with equal or different amplitudes according to appropriate design considerations.

According to a further non-limiting implementation, the corrugated layer can be made by self-assembly or deposited by any other method known in the art, of colloidal or particle matter. The colloid or particle sizes may be uniform or random and may have a size and material chosen according to design considerations.

According to a further non-limiting implementation, the corrugation can be made of a self-affine fractal structure formed by the deposition of a thin metallic film under specific conditions in which the thickness is below or near the percolation threshold, or by any other method known to those skilled in the art.

According to a further non-limiting implementation, a MOIF structure is provided that will support at least one optical mode. The propagating mode may be a waveguide mode, a surface mode, a surface plasmon (SP) mode or a hybrid mode for example. The SP mode can be either propagating or localized according to design considerations.

According to a further non-limiting implementation, the MOIF structure can have an antireflection (AR) layer (or multilayer antireflection coating). The AR layer can be provided on the side of the substrate opposite to one having MO-active material disposed thereon. The exemplary AR layer (or AR coating) will suppress unwanted interference between waves reflected by a side or surface of the substrate opposite to a side or surface having an MO-active layer and waves reflected by a reflecting area of the MOIF adjacent to the MO active layer.

According to a further non-limiting implementation, the exemplary MOIF structure may have a reflective layer (or high reflectance multilayer) contiguous with an MO-active layer in order to provide sufficient reflection of the light from the interface.

According to a still further exemplary implementation, the MOIF structure may have a protective layer disposed adjacent to an object to be tested (i.e., at the "device under test" or "DUT" interface of the MOIF structure).

According to a still further exemplary implementation, the MOIF structure may have at least one layer of material chosen to improve the propagation properties of the optical mode(s) supported by the MOIF structure.

The exemplary MOIF structure design described herein can be applied to nondestructive, real-time characterization of magnetic domain structures for technologically important magnetic materials and devices, such as spin-valves, ultra-thin multilayers, granular systems, permanent magnet quality control, integrated circuit (IC) electrical current visualization, magnetic flux visualization, and to the investigation of superconductors, among many other applications The exemplary MOIF structure described herein can find applications in polarized microscopes, laser scanning microscopes, or any other optical method known to those skilled in the art utilizing at least one optical polarizer.

BRIEF DESCRIPTION OF THE DRAWINGS

These and other features and advantages of presently preferred non-limiting illustrative exemplary implementations will be better and more completely understood by referring to the following detailed description in connection with the drawings, of which:

FIG. 11b is an SEM image of the MOIF structure as in FIG. 11a;

DETAILED DESCRIPTION OF PRESENTLY PREFERRED EXAMPLE NON-LIMITING IMPLEMENTATION

Figure 2A:
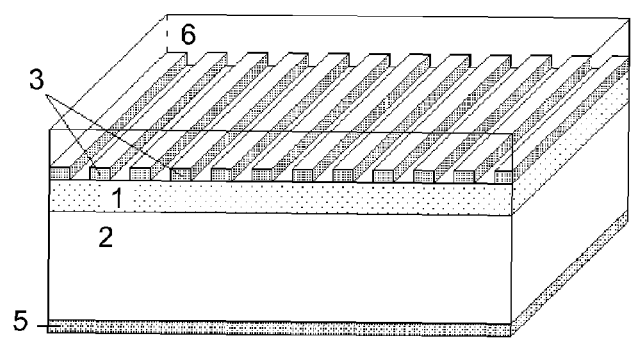
FIG. 2*a* is a diagrammatic perspective view of a first exemplary illustrative non-limiting implementation of a MOIF structure.

As shown in FIG. 2a, an improved exemplary non-limiting implementation of a MOIF structure includes a substrate 2, an at least partially transparent MO-active layer 1, and a metal, one-dimensional grating 3. The MO-active layer 1 may comprise, as a magnetic material in the MOIF, a rare earth iron garnet, an intermetallic compound (for example, MnBi), a non-garnet ferromagnetic oxide (for example, barium-ferrite), a semimagnetic semiconductor (for example, CdMgTe) or any other MO-active and sufficiently transparent material known to those skilled in the art, each as an illustrative non-limiting example. While rare-earth iron garnet (denoted as X:YIG) is generally preferable as a material with both a high Faraday rotation and a sufficient transparency, it should be understood that the technology herein is not to be so limited. Alternatively, two or more layers of similar or different MO-materials can be utilized to enhance magnetic, optical or magneto-optical properties of the MOIF structure. Metal one-dimensional grating 3 may be made of gold, aluminum, silver or copper or any multilayer structure, or composed of layers of gold, silver, aluminum or copper.

The illustrative MO-active layer 1 in the exemplary MOIF structure can exhibit in-plane anisotropy, i.e., the magnetization vector (M) in the MO-active layer is in the plane of the layer in the absence of an external field (such film in the future will be called "in-plane film"). Magnetic fields in the device under test (DUT) 4 may be non-uniform due to, for example, domain structure, current flows, magnetic flux patterns, geometry or other reasons. Such non-uniform magnetic fields cause local rotations of vector M to out-of-plane positions to manifest themselves in the thin MO-active layer 1. Alternatively, the MO-active layer 1 can exhibit so-called easy-plane type magnetic anisotropy. Still alternatively, MO-active layer 1 can exhibit perpendicular anisotropy, i.e. the magnetization vector in the MO-active layer is directed perpendicular to the plane of the layer in the absence of an external fields (such film in the future will be called "perpendicular film"). Further, alternatively, the MO-active layer can exhibit cubic magnetic anisotropy, with three easy axes lying either in the plane or tilted out the plane of the film at some predetermined angle in the absence of the external field. In addition, a DC bias (in-plane for in-plane films and perpendicular for perpendicular films) magnetic field can be constantly applied to MO-active film 1 to reduce or eliminate the magnetic domains. The value and direction of applied bias field should preferably be defined according to the magnetic properties of the MO-active material and to the magnetic fields to be visualized.

The physical basis of the MOIF structure of FIG. 2a can be understood in light of the physical origin of the Faraday effect itself: It is well known that a magnetic field has a direct effect on the spectrum of an atom or molecule, giving rise to a splitting and specific polarization of spectral lines and bands (Zeeman effect, 1896). In the case of the normal longitudinal effect (i.e., the magnetic field and direction of light propagation through the medium are collinear), the original unpolarized spectral line of frequency $\omega_0$ splits into two lines $\omega_0-\Delta\omega$ and $\omega_0+\Delta\omega$ symmetrically disposed about the central line. The two new lines are circularly polarized in opposite directions. The magnetic field thus has a direct effect on the frequency and intensity of the spectral lines and therefore on the polarizability of the molecules. For left-handed circularly-polarized waves, the medium has the absorption frequency $\omega_0-\Delta\omega$, while for right-handed circularly polarized waves it has the absorption frequency $\omega_0+\Delta\omega$. It follows that polarizabilities, and, through that, the complex refractive indices, of a medium placed in a magnetic field are different for right-handed and left-handed waves in a longitudinal direction. This leads to the rotation of the plane of polarization of light traveling through such a medium. Hence, the magneto-optical Faraday effect has a clear light-molecule interaction origin. The value of the Faraday rotation through a unit length of a medium placed in a magnetic field will thus be proportional to the "light-to-molecule interaction rate", which is proportional to the local value of the electromagnetic field of light at the location of the molecule. It should be noted that "local" is a key word here in this exemplary non-limiting description, since the MO effects are linear optical effects, i.e. the total polarization rotation of light traveling through, and reflected from, the medium is independent of incident light intensity. Thus, when a magnetically active optical material is placed at the interface supporting, for example, surface plasmons, the local electromagnetic field near the interface is known to be dramatically enhanced at the SP excitation conditions. See for example Raether H., *Thin Solid Films*, Vol. 28, (no. 1), July 1975. p. 119. The enhancement can be factor of $10$–$10^3$ in the exemplary grating arrangement shown in FIG. 2a.

Figure 2B:
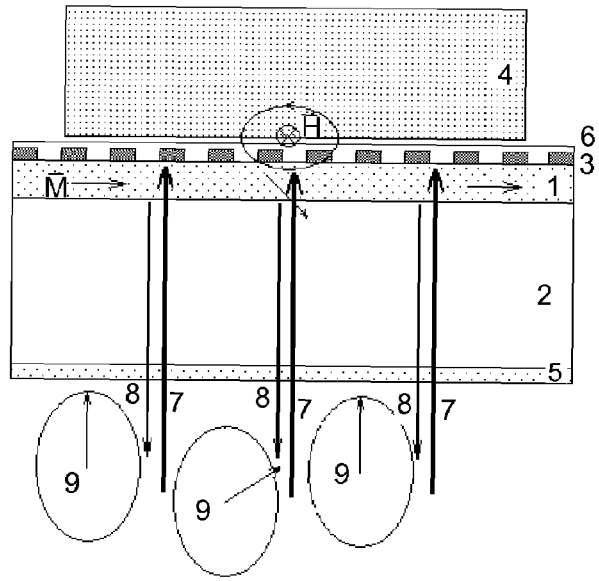
FIG. 2*b* is a schematic view of the FIG. 2 exemplary illustrative implementation of a MOIF structure used with a device under test.
Figure 3:
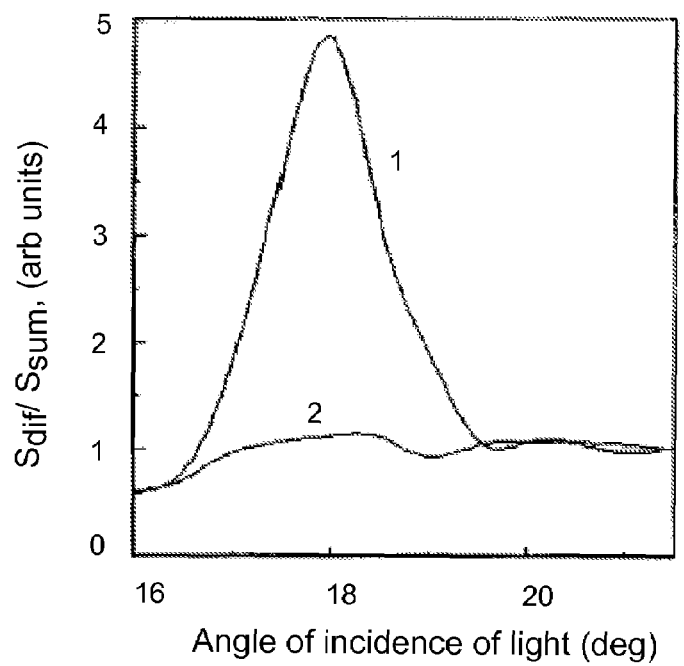
FIG. 3 shows exemplary experimentally measured enhancement of the MO effect near the conditions of SP excitation for the prior art structure examined in Kochergin V. E. et al, *JETP Letters*, Vol. 68, (no. 5), September 1998, p. 400.

In more detail, one exemplary implementation of the MOIF design shown in FIGS. 2a and 2b provides an MO-active layer 1 with magnetic anisotropy chosen according to the discussion given above. This MO-active layer 1 is disposed on optically transparent substrate 2. A periodically corrugated thin Ag or Au layer (60–100 nm thick) 3 is deposited on top of the MO-active layer and then covered by a protective layer 6. The surface of the substrate 2 away from the device under test (DUT) 4 is coated with an antireflection layer 5 in this non-limiting example to eliminate or reduce parasitic interference between the light reflected by the surface of the substrate 2 and the metal layer 3.

The period of the corrugation in the Au or Ag layer is preferably chosen from $$k_{sp} = \frac{\omega}{c}\sqrt{\frac{\varepsilon_m \cdot \varepsilon_d}{\varepsilon_m + \varepsilon_d}} = 2\pi l/\Lambda,$$

where $\omega$ is the frequency of light, $\Lambda$ is the period of grating l is the diffraction order, $\varepsilon_m$ is the dielectric permittivity of metal (Au or Ag) and $\varepsilon_d$ is the dielectric permittivity of MO-active material in MOIF structure. This value of period will cause Surface Plasmon Resonance (SPR) excitation that is exactly normal to the plane surface. For the conditions of first order diffraction, $\Lambda$ should be in the range of 300–400 nm, well accessible for the current holographic lithography tools and state of the art projection photolithography tool. For second order, $\Lambda$ will be about 700 nm—which can be easy produced by standard, fairly inexpensive photolithography with phase-masking. The amplitude of corrugation is preferably chosen to maximize the light coupled into the Surface Plasmon (SP) and to maximize the light reflected out of the SP excitation (~80–90%). The thickness is estimated to be about 7 to 20 nm (depending on particular metal chosen to provide SPs and on the wavelength of illuminating light).

The FIG. 2a exemplary illustrative structure exhibits two interesting physical phenomena that take place on the boundary between the SP-supporting metal (i.e., Au, Ag) and magneto-optically active material. First, a remarkable enhancement of the polarization rotation of reflected light occurs, and second, the behavior of the phase of light reflected from the SP-supporting structure is greatly changed.

Polarization Rotation Enhancement in Reflected Light

Figure 4A:
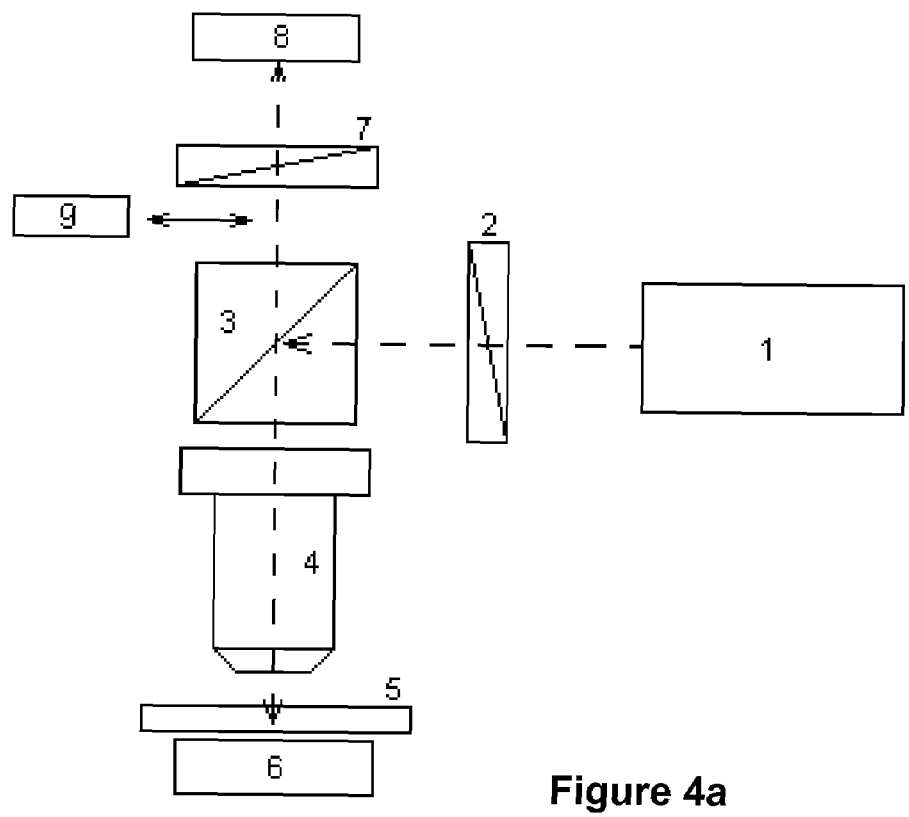
FIG. 4*a* is a schematic drawing of an illustrative exemplary non-limiting implementation of a high-spatial resolution magneto-optical visualizer.
Figure 4B:
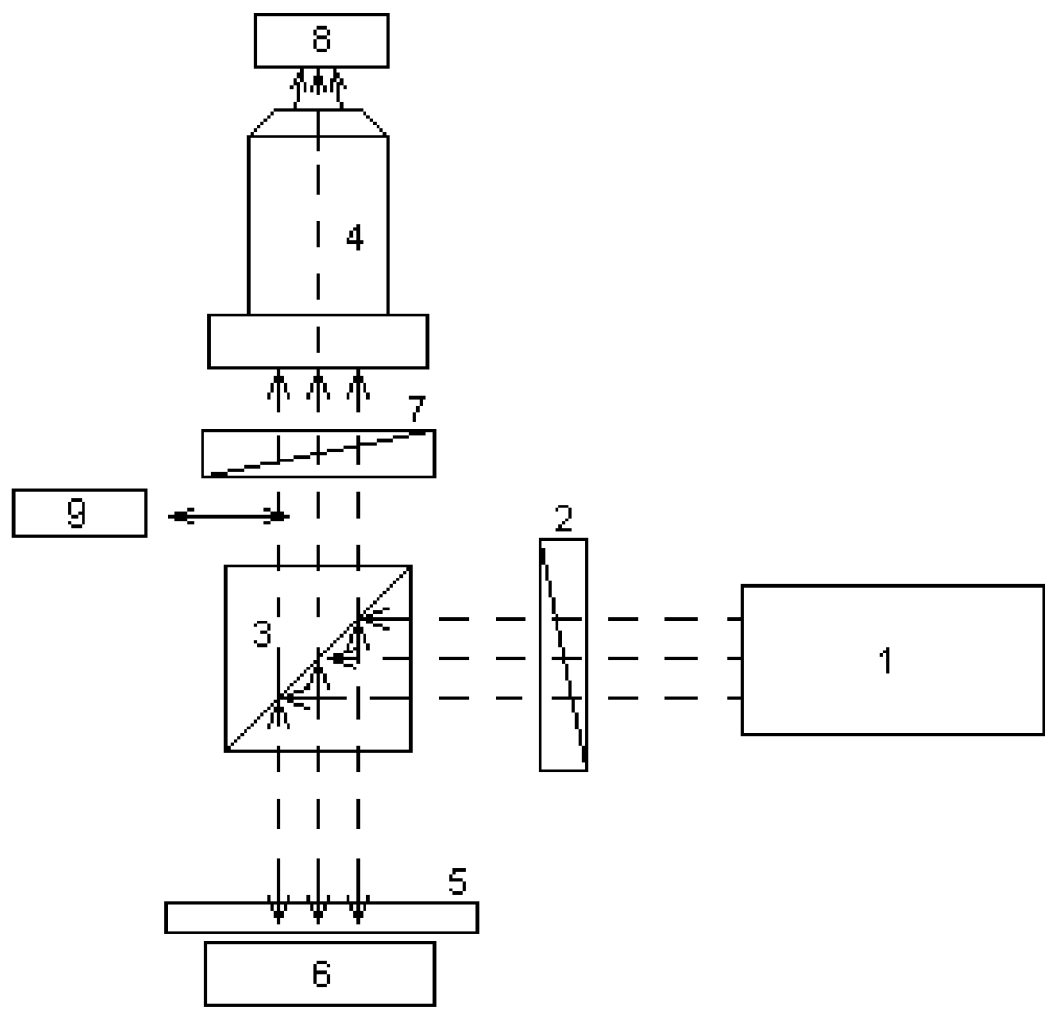
FIG. 4*b* is a schematic drawing of a non-limiting illustrative exemplary implementation of a wide field-of-view magneto-optical visualizer.

The first phenomenon is the remarkable enhancement of the polarization rotation of light reflected from such a structure as described in Safarov V. I. et al, *Physical Review Letters*, 73 (26), December 1994. p. 3584–7, and Kochergin V. E. et al, *JETP Letters*, Vol. 68, (no. 5), September 1998, p. 400. By way of further illustration, FIGS. 4a and 4b show high spatial resolution and wide field-of-view visualizers using the FIG. 2a structure. The components shown in FIG. 4a include:

1—light source;
2—polarizer;
3—beam splitter;
4—microscope objective;
5—MOIF structure;
6—sample under test;
7—analyzer,
8—camera or imaging optics for visual observations, and
9—birefringent plate that can be optionally inserted for phase-sensitive detection As a non-limiting example, a laser can be used for light source 1 if high field resolution is desired. A laser will generally be preferable in this case because the intensity of light at each point of the surface would be ~2–10 mW for a laser, while it would not be more than 100 W/1,000,000 pixels=0.1 mW/pixel with an extremely powerful lamp. Moreover, a laser scanning technique can be made intensity-independent (absolute) by measuring the intensity of a reference beam at frequent intervals. As a further non-limiting example, the visualizers shown in FIGS. 4a and 4b can also employ monochromatic, collimated incoherent light, such as a lamp with an interference wavelength filter and collimating optics.

Further, for the high spatial resolution visualizer (FIG. 4a), the interrogating light is linearly polarized by the polarizer 2 and then deflected by the beam splitter 3 into the objective 4. The light is focused by the microscope objective 4 onto the MOIF structure 5, which reflects it.

For the high field-of-view visualizer (FIG. 4b), a light source 1 passes light through a polarizer 2 to strike a beam splitter 3. The beam splitter 3 deflects some of the light to a MOIF structure 5. The MOIF structure 5 is interfaced with a device or sample under test 6, and reflects light back to the beam splitter and onto the microscope objective 4, this reflected light having a polarization state that is dependent on the MO effect occurring in the MOIF structure 5. A polarizing analyzer 7 can be used to automatically analyze the reflected light. A video camera or imaging optics 8 can be used for visual observations. A birefringent plate 9 can be optionally inserted for phase-sensitive detection.

Figure 1:
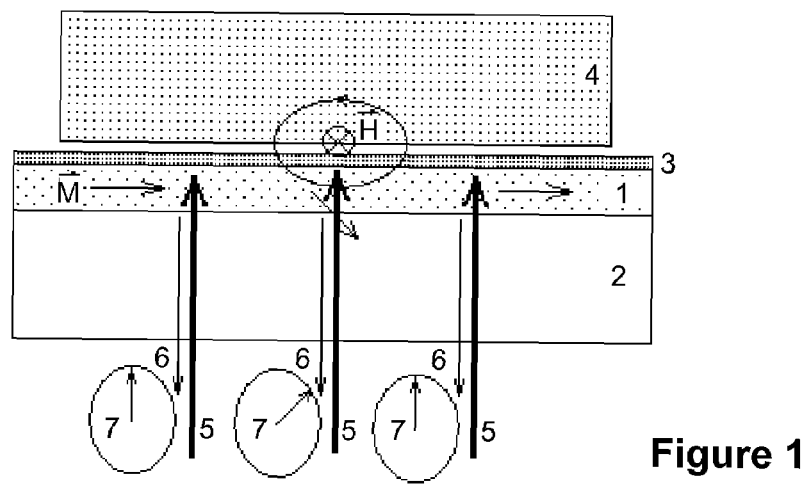
FIG. 1 is a schematic view of an exemplary illustrative prior art MOIF structure.

Since the rotation is non-reciprocal in the FIG. 4b exemplary arrangement, the rotation adds together in the incident and reflected directions while the polarization is acted upon by the local magnetization in the MO-active layer in the MOIF structure. Optical polarization is rotated in Faraday materials for components of light propagating parallel to the internal magnetization vector in the material. For illustrative purposes only, consider the case of an in-plane MO-active film. When an external field from the DUT 6 exists normal to the plane of the MOIF structure, the magnetization is rotated out-of-plane and interacts with the interrogating light. In areas of the DUT 6 where a normal component of an external field is not present, rotation is absent and reflections from these areas (see FIGS. 1 and 2b) have the same polarization as that of the incident beam. This light is extinguished by the analyzer 7, which is crossed with the polarizer 2, producing dark areas. In areas where a normal component of magnetization is present, polarization of the reflected beam rotates with respect to the incident beam, and the amount of rotation (and hence the brightness) depends on the value of the normal component of magnetization. The exact orientation of the analyzer 7 with respect to the polarizer 2 can be chosen to obtain maximum contrast in the image. The function of optional birefringent plate 9 is discussed below.

The physical basis of this effect is believed to be as follows: A SP is a non-radiative surface wave that exists at the interface of a metal and a dielectric. See Raether H., *Thin Solid Films*, 28, (1), July 1975. p. 119. By adding additional momentum via a grating, it is possible to achieve coupling between the incident light and this interface eigenstate. The intensity of light in this case is dramatically enhanced in the vicinity of the interface (1600 times in the prism scheme and up to 10,000 times in the grating scheme). Further, if one of the media forming the SP-supporting interface is Faraday-active, a SP having transverse magnetic (TM) polarization will become elliptically polarized. See Wallis R. F. et al, *Physical Review B* (Solid State), 9 (8), April 1974. p. 3424. Conversely, the transverse electric (TE) component of the SP is proportional to the Verdet constant of the SP and to the total electromagnetic field of the SP. Hence, the TE component will also experience enhancement. Thus, light, re-radiated by the SP, will experience polarization rotation with respect to the light coupled into the SP. This rotation is proportional to the field-enhancement factor of the structure. In the visible wavelength range, an optimized structure can produce between one and two orders of magnitude enhancement. This expectation is consistent with experimental results reported in Kochergin V. E. et al, *JETP Letters*, Vol. 68, (no. 5), September 1998, p. 400. Since MOIF structures will of necessity be thin, the additional MO effects are useful and advantageous.

Phase Behavior of Reflected Light

A second physical phenomenon upon which the FIG. 2a MOIF structure is based is the behavior of the phase of light reflected from the SP-supporting structure. SPR interferometry based on this phenomenon has been recently applied to biological and chemical sensing (see for example Nikitin P. I. et al, *Sensors and Actuators B* B54 (1–2), January 1999 p. 43); and microscopy and visualization (see for example Gigorenko A. N. et al, *Appl. Phys. Lett.*, 75 (25), December 1999. p. 3917; and Notcovich A. G. et al, *Appl. Phys. Lett.* 76 (13), March 2000. p. 1665). This phenomenon, which has aided biological and chemical sensing so much, can also be use in magnetic sensing.

If there are changes in the refractive index or thickness of the media surrounding the SP-supporting interface, the resonance dip is shifted. Thus, when the angle and the wavelength are fixed at the resonance, areas with differing coating thickness or refractive index (see Rothenhausler B.; Knoll W., *Nature*, 332, (6165), April 1988. p. 615) yield different levels of reflected intensity, giving rise to the contrast observed.

Figure 5A:
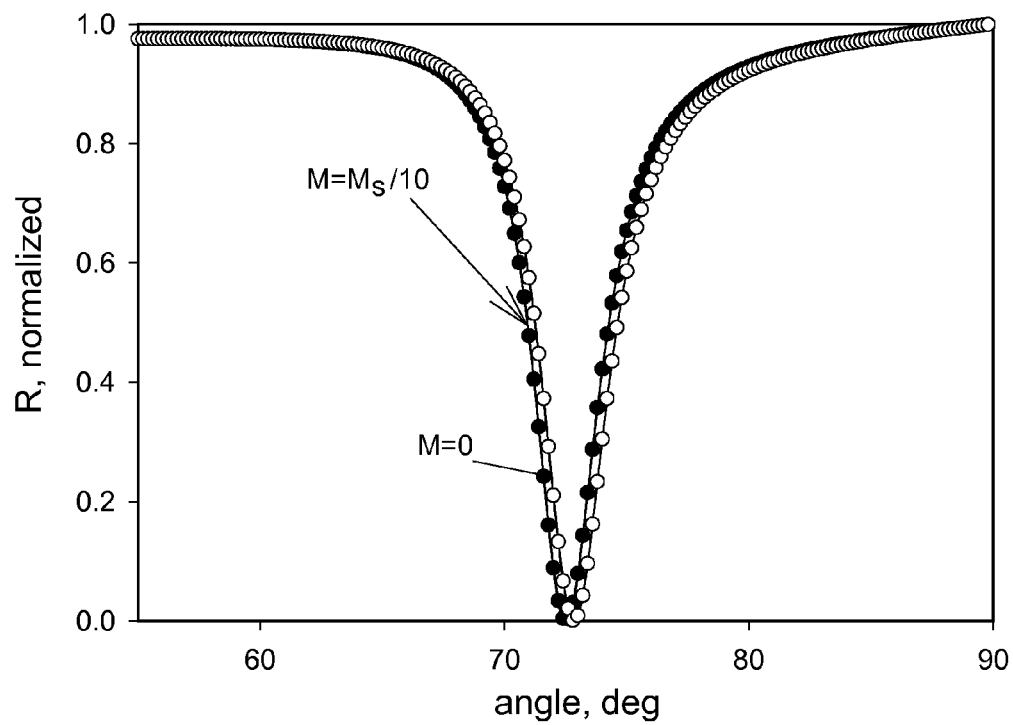
FIG. 5*a* is an exemplary illustrative plot of exemplary numerically calculated reflectivity, R, from a MOIF structure near the SPR conditions in an example Kretchmann (prism) design as a function of the angle of incidence for different magnetizations of a magneto-optically active layer.
Figure 5B:
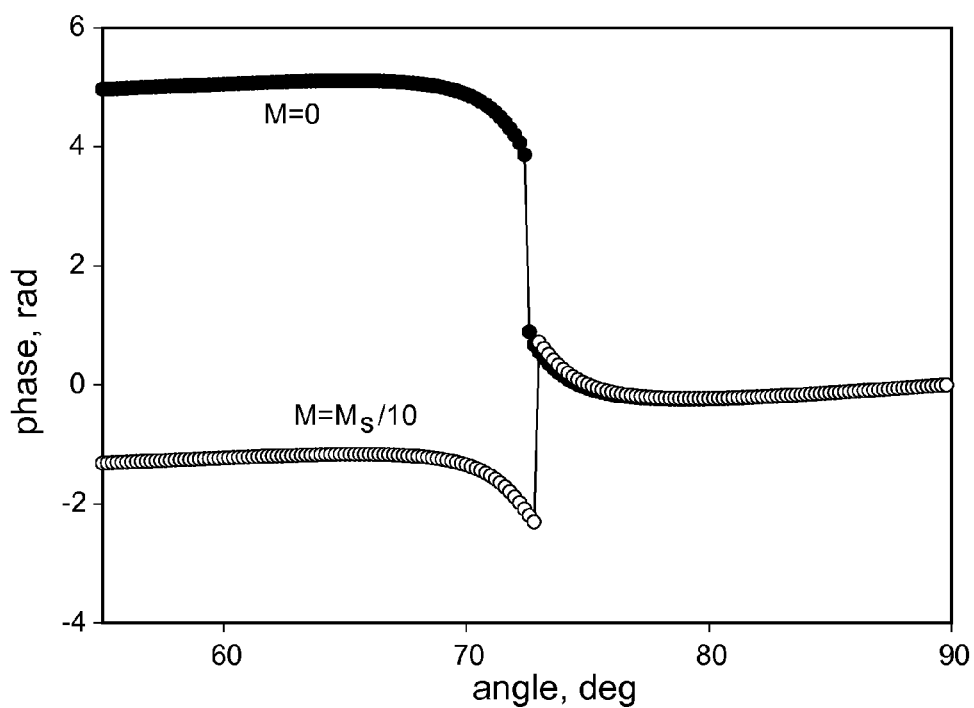
FIG. 5b is an exemplary illustrative plot of numerically calculated phase of waves reflected from a MOIF structure near the SPR conditions in an example Kretchmann (prism) design as a function of the angle of incidence for different magnetizations of the magneto-optically active layer, showing how the phase will flip from the curve with dark circles to the one with open circles with small changes in external field (step change)
Figure 5C:
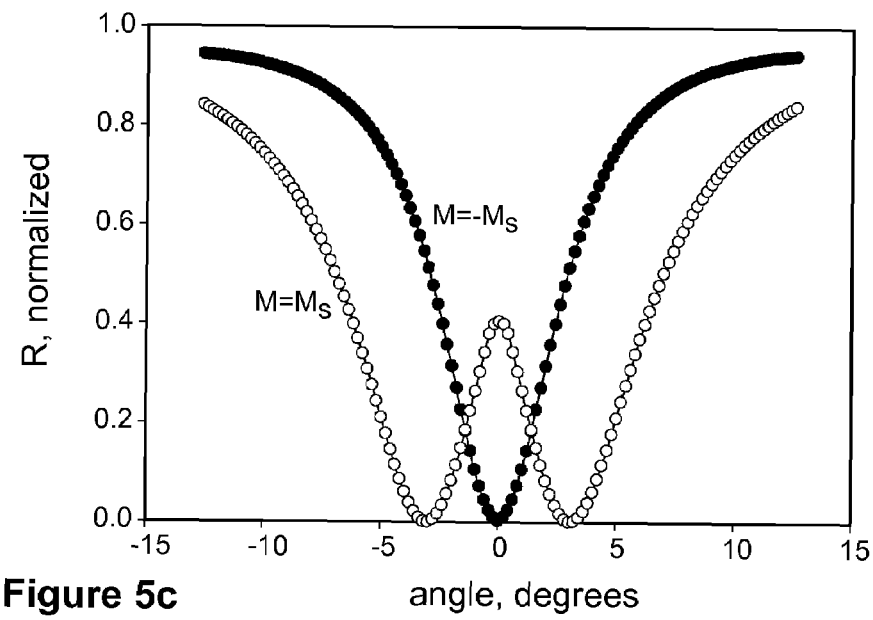
FIG. 5c is an exemplary illustrative plot of numerically calculated reflectivity, R, from a MOIF structure near the SPR conditions in an example grating implementation (see FIG. 1) as a function of the angle of incidence for example different magnetizations of the magneto-optically active layer.
Figure 5D:
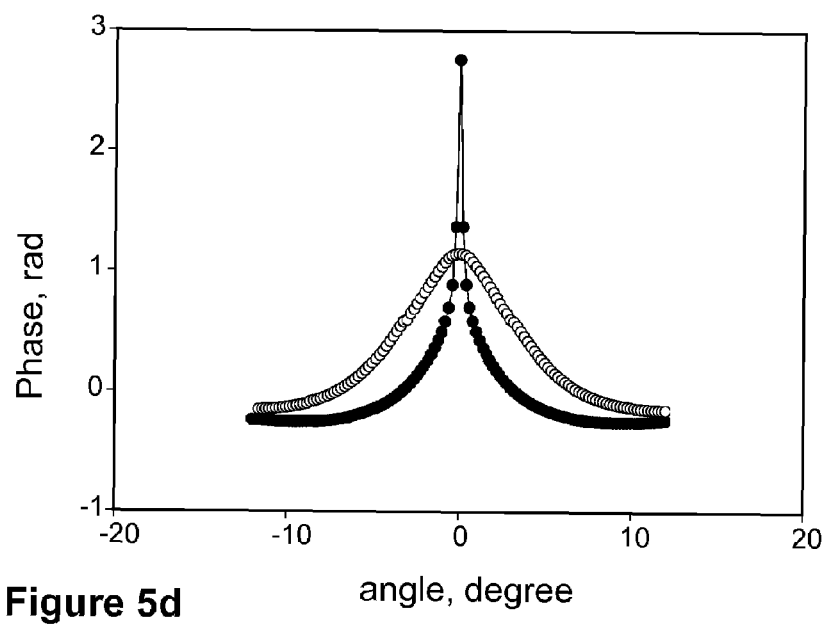
FIG. 5d is an exemplary illustrative plot of numerically calculated phases of waves reflected from an example MOIF structure near the SPR conditions in the grating design of FIG. 2a–2b as a function of the angle of incidence for example different magnetizations of the magneto-optically active layer, showing how the phase will flip from the curve with dark circles to the one with open circles with small changes in external field (step change)

As shown in Kochergin V. E. et al, *Quantum Electronics*, May 1998, 28 (5), p 444, phase variations of reflected light under the variation of system parameters can change much more abruptly than intensity due to the almost Heaviside step-function behavior of the phase as shown in FIGS. 5b and 5d (see Grigorenko A. N. et al, *Optics Communications*, 174 (1–4), January 2000. p. 151). It is well known that changes in the magnetization in the magneto-optical layer are accomplished by changes in the dielectric permittivity tensor. Such changes depend on the orientation of the light direction and polarization, as well as the magnetization direction. In general, non-diagonal elements of the tensor appear when the material is magnetized. The Faraday rotation is directly proportional to the non-diagonal elements of the MO-active material's tensor. For example, for X:YIG as a MO-active material, with rotation about 60,000 degrees/cm, the magnitudes of the non-diagonal elements may reach 10–15% of the diagonal element value. Changes in the wave vector of the SP are generally ~2 times smaller. Exemplary reflectivity and phase of the FIG. 2a MOIF structure with different magnetizations are shown in FIGS. 5a–5d.

In general, the amplitude, phase and polarization of the light reflected from the MOIF structure under SPR conditions will be altered, and an SPR-caused enhancement of the contrast will take place. To take advantage of the changes of all of these parameters, it is desirable to make a small modification to the basic structure of a typical conventional polarizing microscope. For a nonlimiting example of the possible change in microscope configuration that can be made, one more element, a birefringent element 9 (see FIGS. 4a–b), may be added. The birefringent element 9 can, for example, be a quarter-wave plate made from Iceland Spar or other suitable material. The birefringent element 9 serves to break apart the 's' and 'p' components of the light. ('p' is standard notation for light polarized in the plane of incidence, and 's' is the component polarized at right angles). Additionally, analyzing the shape of the interference pattern at the boundary can give precise information about the magnetization distribution within a domain wall by the position and shape of the interference fringes over the area of domain wall.

Figure 6:
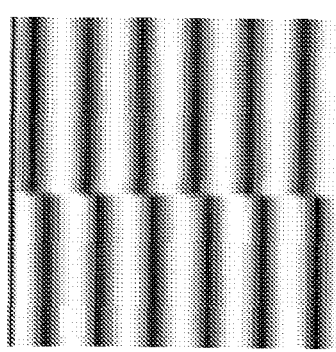
FIG. 6 is an exemplary illustrative plot of an example numerically calculated MOIF image of a spin-valve domain wall showing phase detection due to the MOIF structure of FIG. 2a–2b.

An example of the type of image obtainable with this technique for modest material properties (of, for example, X:YIG) can readily be numerically calculated. An illustrative numerically calculated image of an exemplary spin-valve domain wall visualized using a phase sensitive detection scheme is shown in FIG. 6. In this illustrative nonlimiting example, the MO-active layer was assumed to be Bi:YIG with a modest Faraday rotation of 0.5000 deg/cm at the 632 nm (HeNe red line) wavelength. As shown in FIG. 6, the exhibited contrast between the bright and the dark interference fringes is independent of the MOIF structure's properties and is limited only by the polarizer/analyzer extinction, while the intensity in the bright areas is on the order of 10–20 percent of that of the light coming initially from the light source.

The MO-active layer in the exemplary MOIF structure should preferably exhibit a number of magnetic and magneto-optical properties to have good resolution. The magnetic properties of MO-active layer in MOIF should preferably be defined by the particular application. For example, spin-valve applications may generally require the visualization of fields in the range 1–800 Oe, permanent magnet quality control may generally require visualization of fields of about 1–3 kOe and IC current visualization may generally require the detection of fields well below 1 Oe. The spatial resolution requirements are also different for different applications. For IC current visualization, for example, the required spatial resolution should preferably be high (below 0.5 µm), while superconductor flux visualization may require resolution of only on the order of about 10–100 µm.

As a non-limiting example, consider X:YIG as an MO-active material. Generally, the best-developed method of X:YIG growth is typically liquid phase epitaxy (LPE). It can yield excellent magnetic properties over a wide range of compositions, although there is a strong limitation on the amount of Bi substitution attainable to about 1.5 times that of the yttrium concentration (Bi:YIG). Two alternative techniques are pulsed laser deposition (PLD) (see e.g., Chern M. Y. et al, *Japanese Journal of Applied Physics*, Part 1, 38 (12A), December 1999, p. 6687); and wet chemical processing (sol-gel techniques in particular—see e.g., Uhlmann D. R. et al, *Journal of Non-Crystalline Solids*, 196, March 1996. p. 26)). By using PLD epitaxy, completely substituted $Bi_3Fe_5O_{12}$ has been obtained with a Faraday rotation of −230,000 deg/cm and +440,000 deg/cm at 516 and 443 nm, respectively. The magnetic properties of PLD-grown YIGs are usually inferior to those of LPE-grown YIGs, so LPE is the most common technique for X:YIG layer growth. The sol-gel technique also can provide the potential for obtaining complete bismuth substitution for yttrium, or x=3 YIG (see e.g., Uhlmann D. R. et al, *Journal of Non-Crystalline Solids*, 196, March 1996. p. 26). The sol-gel magnetic properties were also generally better than those of PLD films. The coercivity may be less than 100 Oe, while the saturation field can be in the range of several kOe.

The magnetic properties of YIG are essential for visualization. To understand the magnetic properties of YIG crystals, we can consider first what energies are contributing to the overall YIG film anisotropy. There follows a short exemplary non-limiting list of the different energies with a brief explanation of each:

Exchange energy density, $E_X = A \cdot [(\nabla \alpha_1)^2 + (\nabla \alpha_2)^2 + (\nabla \alpha_3)^2]$, where A is the exchange parameter, determined by the interactions between different YIG sublattices, and $\alpha_1$, $\alpha_2$, $\alpha_3$ are the directional cosines of the orientation of the local magnetization.

Demagnetization energy density, $E_D$, which for the particular thin film YIGs used for MOIF can be approximated with good accuracy by $E_D = 2\pi M_s^2$ when the magnetization is oriented perpendicular to the films and 0 when it is in-plane ($M_s$ is the saturation magnetization of the YIG film). This energy corresponds to the effective demagnetizing field of $H_D = -4\pi M_s$, the magnetization directed into the plane of the film.

Magnetic field energy density $E_H = -M_s \cdot H = -Ms \cdot H \cdot \cos \theta$, where H is the applied field and $\theta$ is the angle between the applied field and the magnetization.

Magnetoelastic energy density $E_S$, which for (111) films is equal to $E_S(111) = \frac{1}{2}\lambda_{100}\sigma_0 + \lambda_{111}\sigma_0(\alpha_1\alpha_2 + \alpha_2\alpha_3 + \alpha_3\alpha_1)$, where $\lambda_{100}$ and $\lambda_{111}$ are the magnetostrictive coefficients of the film material and represent the strain that is induced in a YIG crystal when magnetized to saturation in the (100) and (111) directions, respectively, and local stress in the film $\sigma_0$ is equal to $\sigma_0 = E/(1-v) \cdot (a_0^s - a_0^f)/a_0$, where E is Young's modulus, $v$ is the Poisson's ratio, $a_0^s$ and $a_0^f$ are the lattice parameters of the film and the substrate.

Growth anisotropy energy density $E_K^G = A \cdot (\alpha_1^2 \cdot \beta_1^2 + \alpha_2^2 \cdot \beta_2^2 + \alpha_3^2 \cdot \beta_3^2) + B \cdot (\alpha_1 \cdot \alpha_2 \cdot \beta_1 \cdot \beta_2 + \alpha_2 \cdot \alpha_3 \cdot \beta_2 \cdot \beta_3 + \alpha_3 \cdot \alpha_1 \cdot \beta_3 \cdot \beta_1)$, where $\beta_1$, $\beta_2$, $\beta_3$ are the direction cosines of the growth direction. For (111) films, $\beta_1 = \beta_2 = \beta_3 = \frac{1}{3}^{1/2}$, i.e., $E_K^G = (A+B)/3 + B/3 \cdot (\alpha_1 \cdot \alpha_2 + \alpha_2 \cdot \alpha_3 + \alpha_3 \cdot \alpha_1)$. Simple uniaxial anisotropy with easy axis perpendicular to the film for (111) films occurs when A<0 and B<0.

Crystalline anisotropy energy density, $E_K^C = K_1 \cdot (\alpha_1^2 \cdot \alpha_2^2 + \alpha_2^2 \cdot \alpha_3^2 + \alpha_3^2 \cdot \alpha_1^2) + K_2 \cdot \alpha_1^2 \cdot \alpha_2^2 \cdot \alpha_3^2 + \ldots$ The coefficients $K_1$ and $K_2$ are constants for a given composition and can be either negative or positive depending on the YIG composition. These coefficients in principle define the direction of easy axis (or axes). For example, easy axes coincide with the cubic axes when $K_1 > 0$ and with the cubic diagonal when $K_1 < 0$, but with deviations when $K_2$ is sufficiently large compared to $K_1$.

Crystalline and growth anisotropy energy densities contribute to the anisotropy energy $E_K = E_K^C + E_K^G$. The uniaxial component of the anisotropy energy density is usually expressed as $E_K = K_u \cos^2 \phi$, where $\phi$ is the angle of orientation of the magnetization (i.e. of the easy axis of the film when no external field is applied) and the normal direction of the film. The orientation of (111) is given here as an illustrative non-limiting implementation, but other film orientations can be used instead. In order to obtain an in-plane film, the demagnetization energy should generally exceed the anisotropy energy: $2\pi M_s^2 > K_u$. In at least some example implementations, another useful parameter that can be introduced is the perpendicular saturation field $H_a$. This is the field that must be applied in the (111) direction to move the magnetization perpendicular to the film plane.

Each of the coefficients listed above can vary over a wide range depending upon the YIG and GGG compositions. These in turn can be controlled through the melt composition, liquid phase epitaxy (LPE) and for other process parameters. This leads to the potential for creating many different types of anisotropies through tuning one or more growth parameters.

As has been taught here and by others, there are generally two main applications of MOIF, low field visualization and relatively high field visualization. For low field visualization, potentially the best composition in one exemplary non-limiting implementation will be $Bi_xY_{3-x}Fe_{5-y}Ga_yO_{12}$ where x should be as close to 3 as can be achieved. The amount of Ga should preferably be chosen to minimize $H_k$ and maximize rotation. Higher Ga concentration provides softer magnetic properties, but also leads to decreased rotation. Ga substitution should preferably be 0.3 or lower. The GGG substrate can be chosen to have (111), (110b), (210) or any other orientation to provide needed anisotropy of the iron garnet layer. Lattice matched substrates (GGG with substitutions) are preferred, since more Bi can be inserted into the YIG, thus causing higher Faraday constant. However, since Bi also is responsible for the enhancement of optical absorption in the visible spectral range, lattice matched substrates may at times be dispensed with. In addition, lattice mismatch caused stress that can be utilized to control the magnetic properties of iron garnet films. For high field visualization, the composition will be determined by the particular application. For the analysis of spin-valves, for instance, pure Bi:YIG with $M_s = 1600$ G on specially matched substrates can be used, since it has the lowest optical absorption and the highest rotation. Annealing in a high magnetic field can provide lower absorption and/or other desired changes to the anisotropy.

The coercive force, $H_c$, generally does not contribute anything directly to the MOIF signal. It can, however, be used for avoiding the demagnetization of the MO-active material in MOIF structures at the highest fields to be used for a given application. For visualization of some dynamic processes like spin-valve magnetization or magnetic-flux redistribution in superconductors, $H_c$ should be smaller than the maximum field to be detected, $H_m$.

Figure 7:
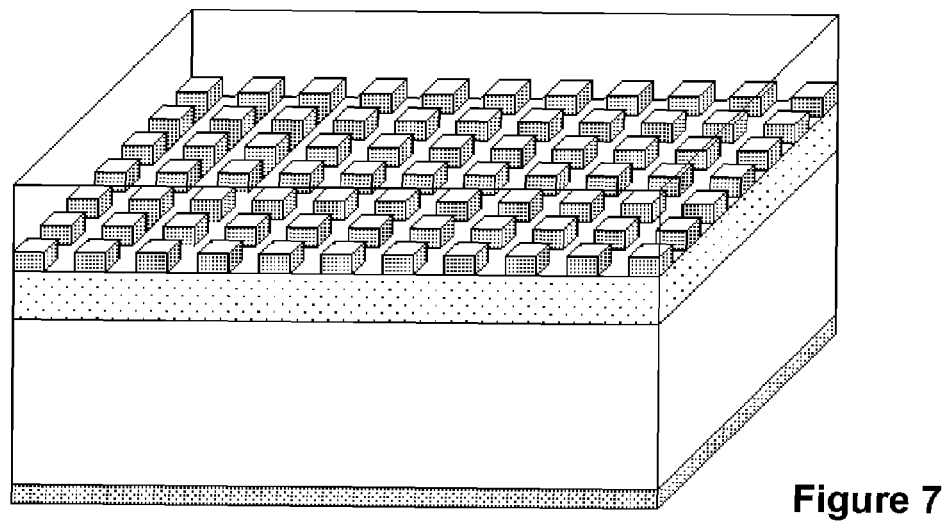
FIG. 7 is a diagrammatic perspective view of an exemplary illustrative non-limiting MOIF structure implementation having a two-dimensional diffraction grating formed into a metal layer.

It should be noted that although corrugation in the form of one-dimensional diffraction gratings is shown in FIG. 2a, it is also possible to use corrugation in the form of two-dimensional diffraction grating as shown in FIG. 7. A two-dimensional grating can, for example, be formed by superposition of any number of non-collinear one-dimensional gratings with equal or different amplitudes of corrugation and with equal or different periods. Each grating in such a superposition array can be characterized by its wavevector $K_i = n_i 2\pi/\Lambda_i$ where i is describe the grating number, $n_i$ is a unit vector in the direction of grating wavevector and $\Lambda_i$ is the period of grating. In this case, the SP excitation conditions will take the form $$k_{sp} = \frac{\omega}{c}\sqrt{\frac{\varepsilon_m \cdot \varepsilon_d}{\varepsilon_m + \varepsilon_d}} = |\Sigma K_i|,$$

where the sum is vector sum and is taken with not only all gratings but also with at least ±1 optical orders for each grating. This exemplary non-limiting structure can have advantages over one-dimensional gratings in certain applications due to more than one orientation of the MOIF structure with respect to the polarizer and analyzer, where polarization rotation enhancement occurs. It is also should be noted that a two-dimensional corrugation can have a quasicrystalline type of symmetry. In this case, for example, 12 or more directions of MOIF structures with respect to a fixed polarizer/analyzer can satisfy SP excitation conditions at normal incidence and polarization rotation will be enhanced at almost any MOIF structure orientation.

Although only diffraction gratings formed by corrugation of the surface of some layer within the MOIF structure are shown in FIGS. 2a and 7, it is also possible to use a phase (or refractive index) grating, formed in any layer, in which the SP is at least partially localized. Such a refractive index grating can be written, for example, by pulsed UV laser irradiation through a phase mask into the film of a MOIF structure in which an optical mode is at least partially localized, or by any other technique known to those skilled in art.

Figure 8A:
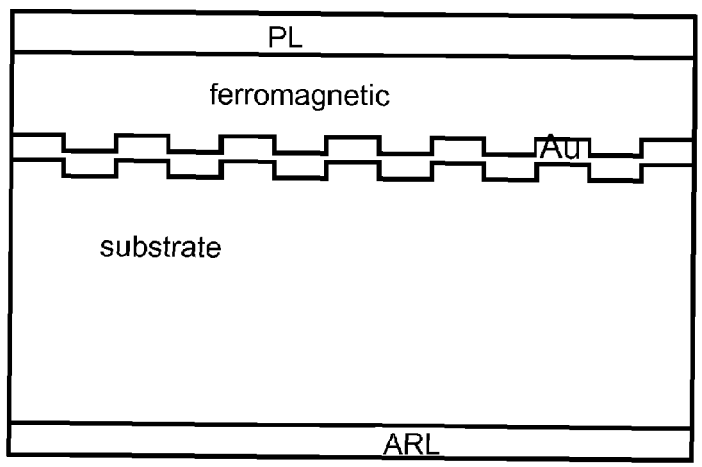
FIGS. 8a–d are illustrative schematic drawings of further exemplary non-limiting MOIF structures.
Figure 8B:
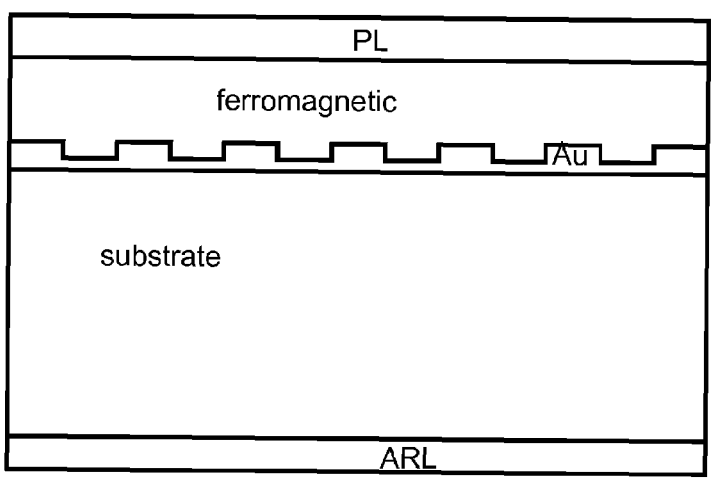
Figure 8C:
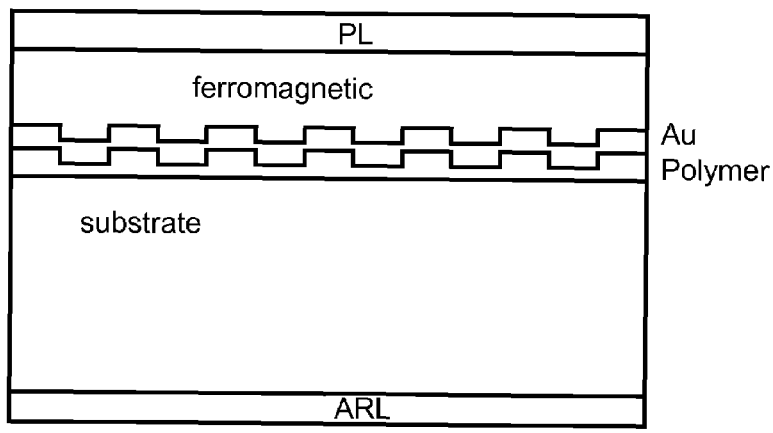
Figure 8D:
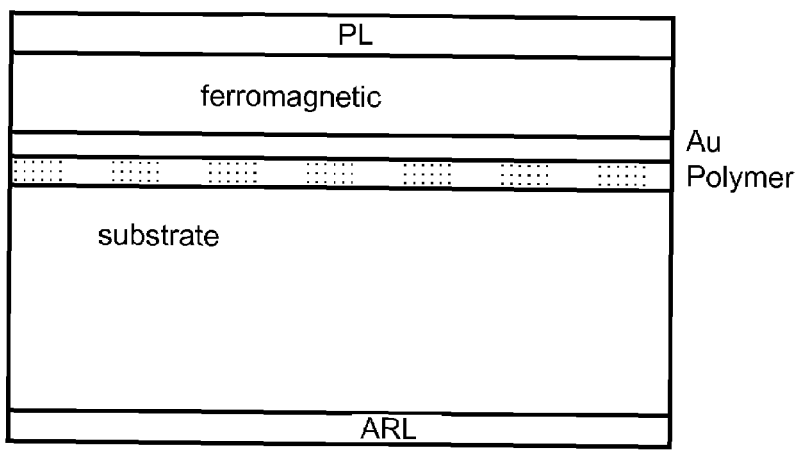

A further exemplary, non-limiting illustrative implementation uses a ferromagnetic MO-active layer of, for example, iron/boron amorphous magnetic alloy, Permalloy, iron, cobalt or any other ferromagnetic material having sufficient MO activity and magnetic properties, suitable for any given particular application. A thin (10–2000 nm) layer of ferromagnetic MO-active material can be applied (e.g., by magnetron sputtering, electroplating, laser ablation or deposition by any other technique known to those skilled in the art) onto a thin (2–15 nm) film of nonmagnetic metal. The thin non-magnetic metal film can be selected from the group consisting of silver, gold, aluminum, or copper. Any number of layers of silver, gold, aluminum or copper metal can be employed (FIG. 8). The nonmagnetic metal can be deposited onto a transparent substrate (FIG. 8a)in a way so as to corrugate it during the deposition process using any technique known to those skilled in the art; or it can be deposited on flat transparent structure and later corrugated by any technique known to those skilled in the art afterwards (FIG. 8b); or it can be deposited on a transparent corrugated polymer layer or multilayer which is then attached in turn onto the substrate (FIG. 8c); or it can be deposited on the flat transparent layer with a phase grating photoinduced by any technique known to those skilled in the art (FIG. 8d).

The polarization rotation in such a structure will experience enhancement based on the same effect that was employed in the FIG. 2a implementation. Strong damping of SP in the ferromagnetic metal in this case will be partially compensated by almost complete absence of damping in the polymer or substrate and thin layer of silver, gold, aluminum or copper. The thickness of this thin nonmagnetic layer should be chosen according to a tradeoff between maximum rotational enhancement factor (proportional to the quality of resonance and, in the first approximation, to the thickness of the nonmagnetic metal layer) and the value of MO effect itself (inversely proportional, in the first approximation, to the thickness of nonmagnetic metal layer). The period of the grating and the amplitude of the corrugation (or the amplitude of refractive index variation for the case of a phase grating) are preferably defined by the same parameters as in the FIG. 2a implementation. The thickness of the ferromagnetic layer should preferably be defined by spatial resolution and magnetic properties requirements. Just as for the FIG. 2a implementation, antireflection and protective layers can be used. Contrary to the FIG. 2a implementation, the protective layer should serve not only for mechanical protection, but also for environmental protection, since most (if not all) of MO-active ferromagnetic materials are reactive and suffer from various atmospheric gas contamination and moisture. Although in this exemplary non-limiting implementation the field resolution will probably be inferior to that of the FIG. 2a implementation, the spatial resolution of such an MOIF structure will not be limited by the thickness of MO-active layer, since the signal is formed by 5–20 nm of MO active layer. The spatial resolution is expected to be superior to a 300 nm MOIF layer in at least some implementations.

Several desirable applications of MOIF structures use visualization at a frequency that is different from the illumination frequency. See for example Reif J, et al. *Phys. Rev. Lett.* 67 (20), p 2878, November 1991. For example, imaging at double the frequency of illumination—also known as second harmonic generation (SHG)—offers high polarization rotation with almost complete absence of the background signal. Another advantage of such a technique is the potential to investigate the magnetic properties on the interface of the MO-active layer in the MOIF structure, which is important from the viewpoint of spatial resolution of MOIF-based devices and instruments.

As well known to those skilled in the art, SP provides strong enhancement of frequency conversion and nonlinear effects due to strong electromagnetic field enhancement. In such conditions, the exemplary MOIF structures discussed above are applicable for visualization measurements at higher harmonics of light. However, even more enhancement of the signal at the converted frequency will take place in the exemplary MOIF structure shown in FIGS. 9 and 10.

Figure 9A:
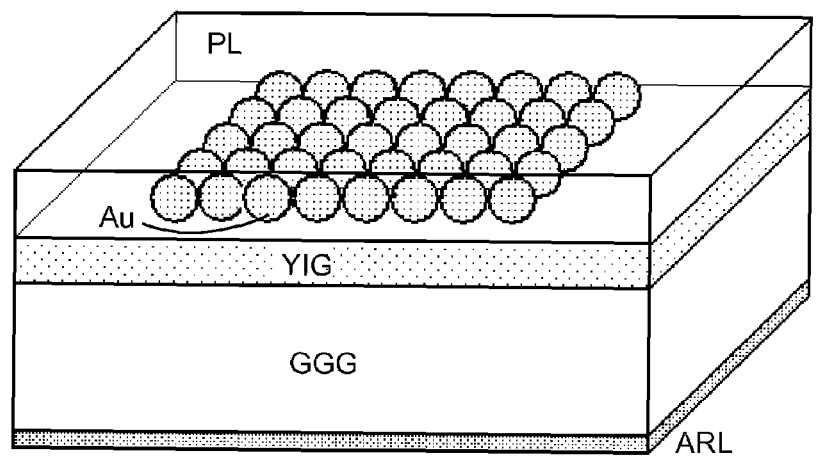
FIG. 9a–c are illustrative schematic drawings still further exemplary non-limiting MOIF structures employing MO-active layers exhibiting a positive real part of dielectric permittivity in the operational wavelength range of the magneto-optical indicator film.
Figure 9B:
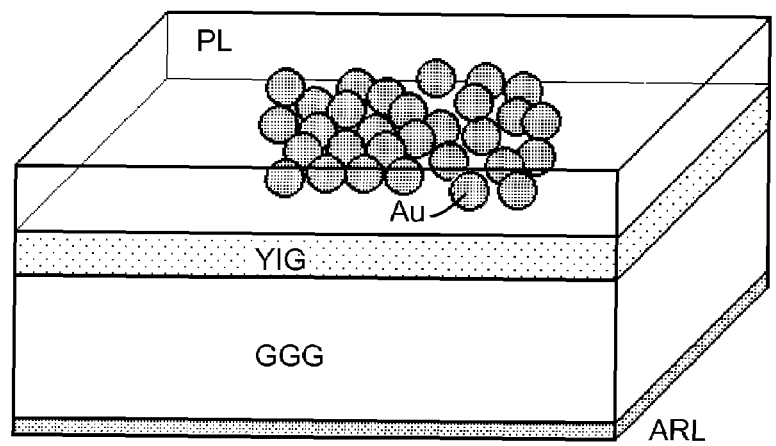
Figure 9C:
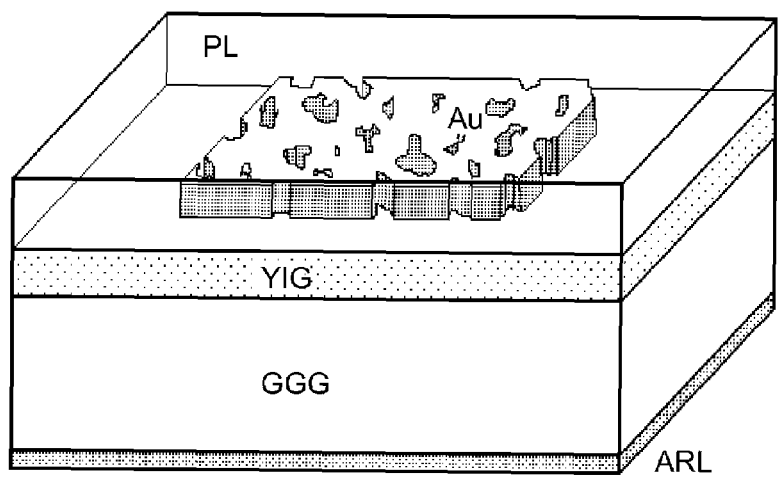
Figure 10A:
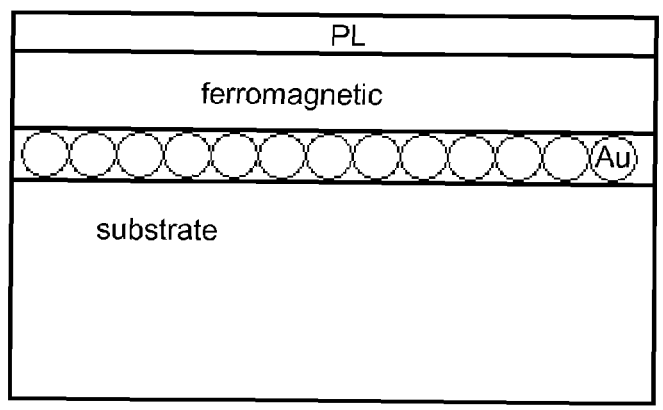
FIG. 10a–b are illustrative schematic drawings of the MOIF structures employing MO-active layers exhibiting a negative real part of dielectric permittivity at the operational wavelength range of the magneto-optical indicator film.
Figure 10B:
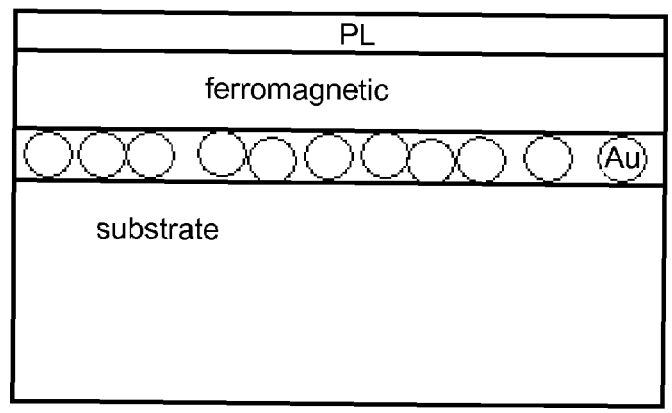

FIG. 9 shows an exemplary relatively transparent MO-active material with positive dielectric constant similar to those described in connection with FIG. 2a. FIG. 10 describes the case of ferromagnetic MO-active material. In both cases, so-called localized SP on the colloids and clusters of nonmagnetic metal (Au, Ag, Al or Cu) are used as providers of such SP's. The signal enhancement in such structures can reach several orders of magnitude. The size and shape of colloids should be chosen to maximize the optical performance of the MOIF structure. Colloids can be disposed by self-assembly, as a nonlimiting illustrative example, while clusters can be magnetron sputtered under special conditions or thermally evaporated. Metal particles can also be incorporated in polymers and then spin-coated.

Alternatively, said metal colloids or clusters can be formed by standard photolithography technique, or by e-beam lithography or Langemuir/Blodgett coating. In the case of MO-active material, similar to those described in connection with FIG. 2a, the metal particles should be disposed on the top of MO-active material (FIG. 9). In the case of the use of ferromagnetic material, a ferromagnetic layer can be deposited on the top of metal colloids and/or clusters. In the exemplary implementation, there is no need to apply an antireflection coating on the opposite side of the substrate since there is no reflected mode from it at a higher order than first harmonic.

Set forth hereafter are details concerning a specific experimental examples showing the advantageous features of the MOIF film fabricated according to selected aspects of an exemplary illustrative non-limiting arrangements. The details of this example may be varied to an extent and are not taken as limiting. This example has been chosen and set forth merely to illustrate and describe the concepts but are not intended to be limiting.

NON-LIMITING EXAMPLES

Figure 11A:
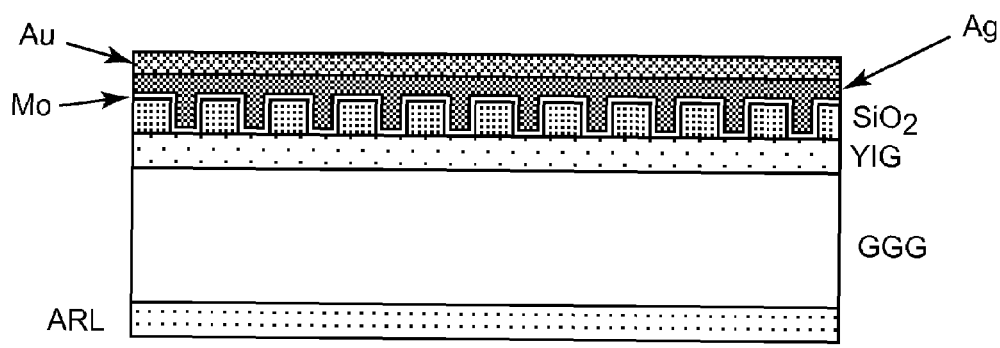
FIG. 11a is a schematic illustrative drawing of an experimentally realized SPR-enhanced MOIF film.

A schematic drawing of one exemplary non-limiting MOIF structure is shown in FIG. 11a. It consists of:
a commercially purchased YIG film LPE-grown on a lattice-matched GGG substrate,
an antireflection coating on the GGG side of the wafer (105 nm of $SiO_2$ RF magnetron-sputtered onto the GGG side for ~600 nm wavelengths),
a diffraction grating etched into said $SiO_2$ layer on the top of the YIG, about 2 nm of RF magnetron-sputtered Mo "glue" layer over the grating (to enhance the adhesion of the following layers to the YIG/SiO2 grating interface), and
an 120 nm thick silver layer RF magnetron sputtered onto the glue layer followed last by a 30-nm protective gold layer sputtered onto the silver layer.

The example grating structure can be fabricated as follows: the to surface of the YIG film is coated with 200 nm of $SiO_2$ by RF magnetron sputtering, and the samples then shipped to a commercial vendor who defines a photoresist grating pattern on the top of SiO2 layer. Then, the samples received back from the commercial vendor may be processed in a reactive ion etcher (RIE) to transfer the photoresist grating pattern into the $SiO_2$ layer. By following this procedure, several MOIF films representative of the exemplary illustrative non-limiting arrangement can be prepared.

Figure 11B:
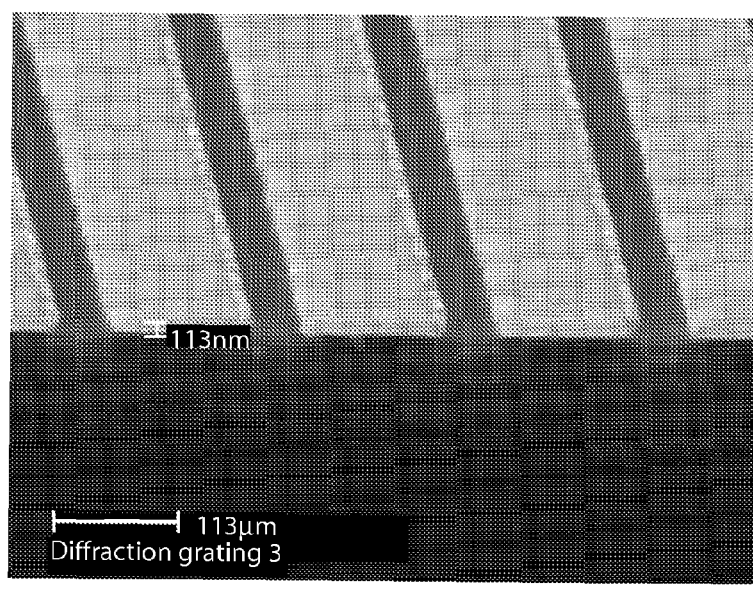

The SEM image of the grating etched into SiO2 layer (before multilayer metal coating) is given in FIG. 11b. To demonstrate the feasibility of the disclosed technique, the visualization of domains and domain walls may be used. The image of the domain wall is located approximately in the center of the grating area. The SPR-enhanced image (FIG. 12a) and is obtained in a reflected-light polarizing microscope (as in FIG. 4a) with a halogen lamp as an illuminator and an orange narrow band-pass filter. The polarizer may be oriented such that the light incident on the sample has TM polarization. The analyzer position may be adjusted to obtain the maximum contrast of the image and the image may then be acquired. To obtain a non-SPR enhanced image (FIG. 12b) the polarizer and analyzer may be set in a fixed position, while the MOIF film is placed on a precise rotation stage and rotated by 90° (so the polarization of incident light became TE) and the image may again be acquired. The enhancement of the contrast caused by SPR is thus demonstrated. The cross-sections of light intensity from both images may be taken perpendicular to the domain wall as presented in FIG. 12c (it should be noted that both curves may be shifted on the vertical (intensity) scale to be distinguishable).

Figure 12A:
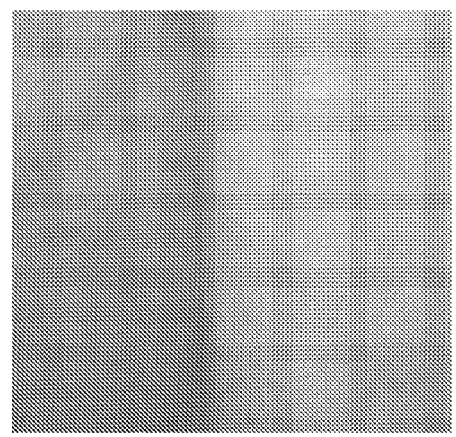
FIGS. 12(a) and 12(b) show SPR-enhanced and non-SPR-enhanced exemplary MOIF images, respectively, of a domain wall (dark vertical line (a)) in perpendicular magnetization YIG; in which cross-sections of both images were taken perpendicular to the domain wall.
Figure 12B:
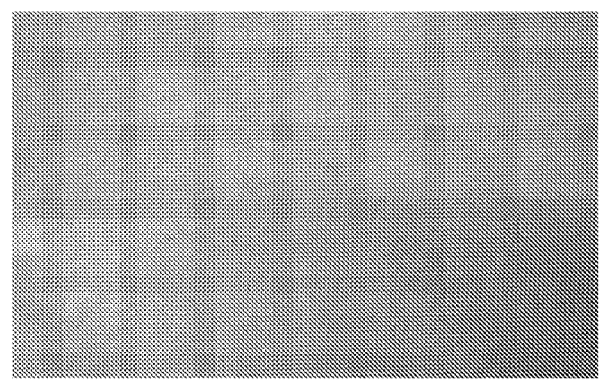
Figure 12C:
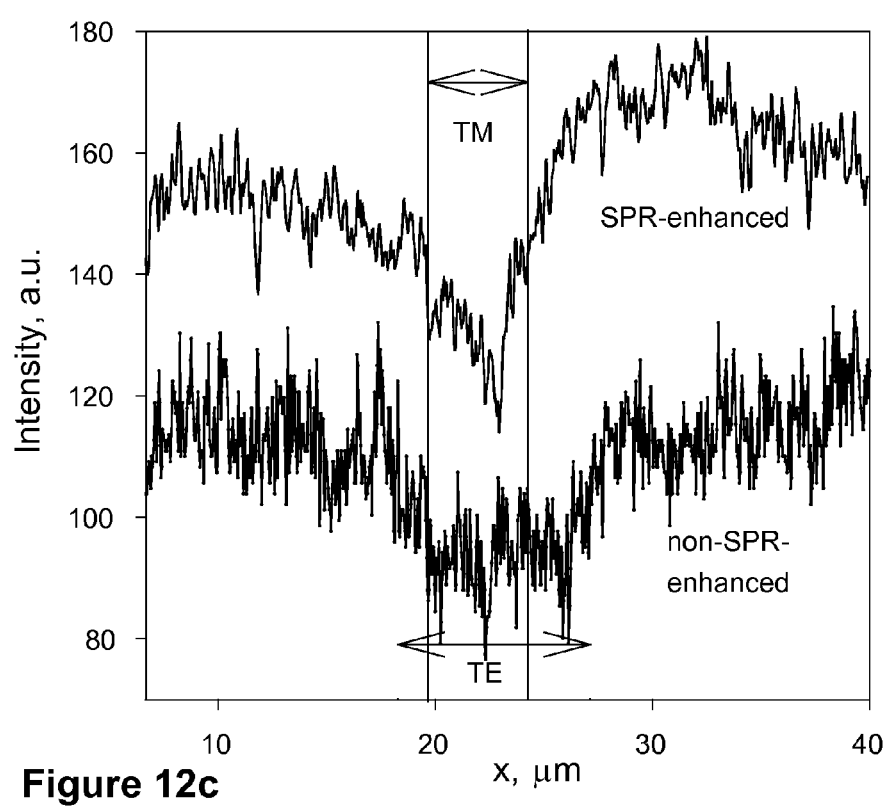
FIG. 12(c) shows an exemplary plot corresponding to FIGS. 12(a) and 12(b)

One can see that not only is the contrast of the domain wall image enhanced in this illustrative non-limiting example, but also the width of the domain wall image becomes smaller. This effect can be explained as follows: The depth of focus of the optical microscope with a 100× objective is much smaller than the YIG film optical thickness (which is 2.3 times larger than the physical thickness of 2.8 μm). In the non-SPR enhanced case, this causes the superposition of the effects from the entire YIG film thickness, thus making the domain wall image considerably wider than it is in reality. With SPR-enhancement, it is possible to focus the microscope right on the YIG-metal interface where most of the signal is generated through SPR enhancement. This provides a much higher contrast image of the domain wall with the visualized spatial dimensions much closer to the actual domain wall width. For this particular film, the actual width may be between 2 and 3 microns. Another conclusion that can be made from FIGS. 12(a)–(c) is that the spatial resolution of the visualizer employing the SPR-enhanced film is demonstrated to be better than 2–3 microns without any parasitic images of the grating grooves.

Figure 13A:
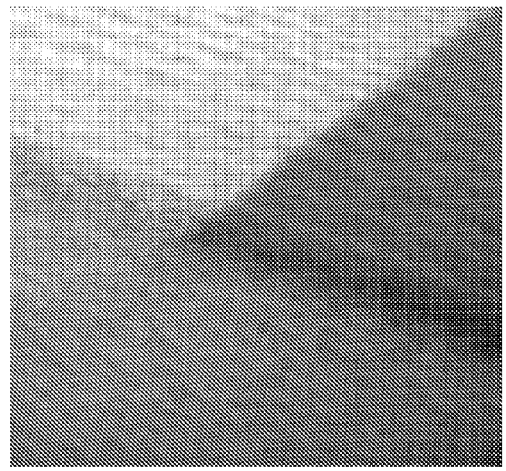
FIGS. 13(a) and 13(b) show example MOIF images of domain and grating boundary intersections with polarizer and analyzer oriented to maximize the domain boundary contrast within and outside the grating areas respectively (cross-sections of both images made perpendicular to the domain boundary)
Figure 13B:
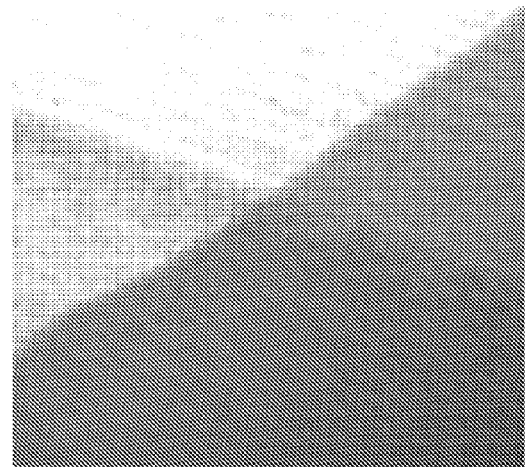
Figure 13C:
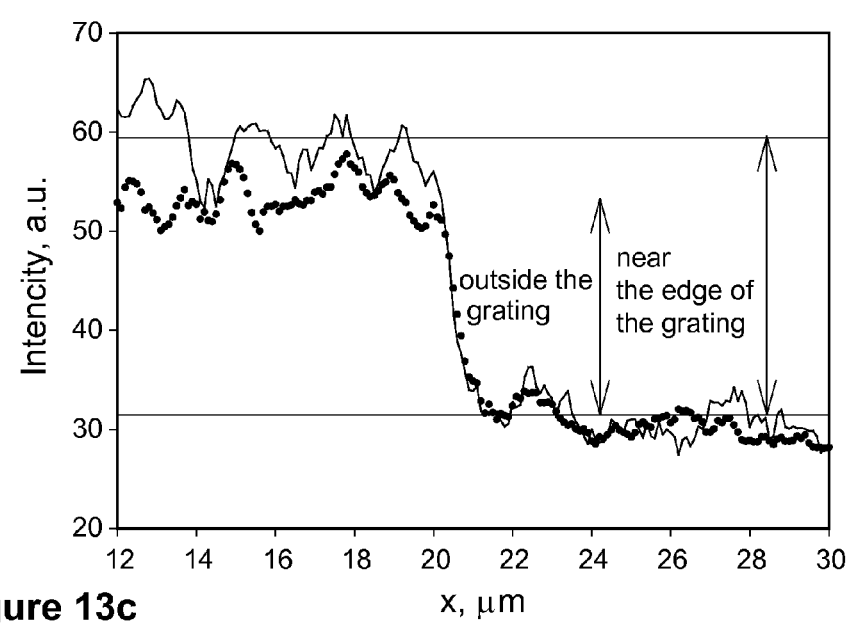
FIG. 13(c) shows an exemplary plot where the dotted curve is the cross section of the domain wall image outside the grating and the arrows measure the approximate average intensity differences between the two sides of the domain wall near the edge of the grating and outside the grating.

The absolute value of the contrast enhancement may be determined in an experimental setup with a somewhat different procedure. In this case, images of the intersection of the domain and grating boundary may be made. The image in FIG. 13a may be obtained by adjusting the polarizer and analyzer positions to visually maximize the contrast of the domain boundary within the grating area while the image in FIG. 13b may be obtained by adjusting the positions of polarizer and analyzer to maximize the contrast outside the grating area. FIG. 13c shows the cross-sections of both images perpendicular to the domain boundary. One can see that the magnetic image contrast enhancement achieved in such an exemplary illustrative structure is ~30%. It should be noted that no thorough optimization of either the grating depth (which determines the SPR quality, i.e. enhancement factor) nor the grating period were made. However, the experimentally obtained contrast enhancement is quite significant, considering that ~5.5 microns of YIG was contributing to the non-SPR image contrast, while only about 200 nm of YIG contributed to the SPR-based contrast enhancement.

While the invention technology herein has been described in connection with what is presently considered to be the most practical and preferred implementations, it is to be understood that the invention is not to be limited to the disclosed exemplary illustrative non-limiting implementations. For example, while periodic corrugation has been disclosed in certain exemplary illustrative non-limiting implementations, other period or non-periodic structural or surface variation patterns are also possible. Systems can operate using reflectance, transmittance or both, depending on the particular application. Different types of gratings can be employed. Different types of magneto-optical materials than those described herein by way of example only could be used in different applications. Different results than those described herein may be obtained for different experimental setups. Therefore, the metes and bounds of invention is defined by the claims—not by this specification—and are intended to cover various modifications and equivalent arrangements included within the scope of the claims.

What is claimed is:

1. A magneto-optical indicator element comprising:
a substrate;
a thin film indicator structure comprising a plurality of thin-film layers disposed on a said substrate, at least one of said layers comprising magneto-optically (MO)-active material having predetermined magnetic properties including magnetic anisotropy, magnetization saturation value, coercive field value; and a magneto-optical effect value; said indicator structure including at least one of said layers having a thickness and/or refractive index modulated in a predetermined fashion; said indicator structure having at least one optical mode which is at least partially localized within and/or at at least one interface of said at least one MO-active layer; said at least one optical mode being at least partially localized in said one layer having modulated thickness and/or refractive index,
further comprising a thin layer of metal having a thickness of no more than 15 nm and selected from the group, consisting of: Ag, Al, Au, Cu disposed contiguous to said layer of ferromagnetic material,
wherein the optical mode comprises a surface plasmon mode and at least one magneto-optically-active layer provides a single surface that supports the surface plasmon mode,
wherein said MO-active layer comprises ferromagnetic material,
wherein said thin layer of metal has a constant thickness, and
wherein said metal layer has a modulated thickness and is disposed adjacent to a thin layer of metal on a side opposite to the MO-active layer.

2. A magneto-optical indicator element comprising:
a substrate; and
a thin film indicator structure comprising a plurality of thin-film layers disposed on a said substrate, at least one of said layers comprising magneto-optically (MO)-active material having predetermined magnetic properties including magnetic anisotropy, magnetization saturation value, coercive field value; and a magneto-optical effect value; said indicator structure including at least one of said layers having a thickness and/or refractive index modulated in a predetermined fashion; said indicator structure having at least one optical mode which is at least partially localized within and/or at at least one interface of said at least one MO-active layer; said at least one optical mode being at least partially localized in said one layer having modulated thickness and/or refractive index;
wherein the optical mode comprises a surface plasmon mode;
wherein at least one magneto-optically-active layer provides a single surface that supports the surface plasmon mode;
wherein said MO-active layer comprises ferromagnetic material;
further comprises a thin layer of metal having a thickness of no more than 15 nm and selected from the group, consisting of: Ag, Al, Au, Cu disposed contiguous to said layer of ferromagnetic material, and
wherein said thin layer of metal has a modulated thickness.

3. The magneto-optical indicator element of claim 2 wherein said thin layer of metal has a constant thickness.

4. The magneto-optical indicator element of claim 3 wherein said metal layer of modulated thickness is disposed adjacent to a thin layer of metal on a side opposite to the MO-active layer.

5. A magneto-optical indicator element comprising:
a substrate; and
a thin film indicator structure comprising a plurality of thin-film layers disposed on a said substrate, at least one of said layers comprising magneto-optically (MO)-active material having predetermined magnetic properties including magnetic anisotropy, magnetization saturation value, coercive field value; and a magneto-optical effect value; said indicator structure including at least one of said layers having a thickness and/or refractive index modulated in a predetermined fashion; said indicator structure having at least one optical mode which is at least partially localized within and/or at at least one interface of said at least one MO-active layer; said at least one optical mode being at least partially localized in said one layer having modulated thickness and/or refractive index,
wherein the optical mode comprises a surface plasmon mode;
wherein at least one magneto-optically-active layer provides a single surface that supports the surface plasmon mode;
wherein said MO-active layer comprises ferromagnetic material;
further comprises a thin layer of metal having a thickness of no more than 15 nm and selected from the group, consisting of: Ag, Al, Au, Cu disposed contiguous to said layer of ferromagnetic material;
wherein said thin layer of metal has a constant thickness; and
wherein a sufficiently transparent layer of material with a spatially modulated refractive index is disposed adjacent to the thin layer of metal on the side opposite to the substrate.

6. The magneto-optical indicator element of claim 5 wherein said layer of modulated thickness is made of transparent dielectric material.

7. A magneto-optical indicator element comprising:
a substrate; and
a thin film indicator structure comprising a plurality of thin-film layers disposed on a said substrate, at least one of said layers comprising magneto-optically (MO)-active material having predetermined magnetic properties including magnetic anisotropy, magnetization saturation value, coercive field value; and a magneto-optical effect value; said indicator structure including at least one of said layers having a thickness and/or refractive index modulated in a predetermined fashion; said indicator structure having at least one optical mode which is at least partially localized within and/or at at least one interface of said at least one MO-active layer; said at least one optical mode being at least partially localized in said one layer having modulated thickness and/or refractive index,
wherein the optical mode is a localized surface plasmon mode;
wherein said localized surface plasmon mode is at least partially localized in the at least one MO-active layer; and
wherein the at least one layer with a modulated thickness is a metal, selected from the group, consisting of: Ag, Au, Al, Cu.

8. The magneto-optical indicator element of claim 7 wherein the thickness modulation is made in the form of self-assembled ordered colloids made of metal selected from the group consisting of: Ag, Au, Al, Cu.

9. The magneto-optical indicator element of claim 7 wherein the thickness modulation is made in the form of self-assembled, unordered colloids made of metal selected from the group consisting of: Ag, Au, Al, Cu.

10. The magneto-optical indicator element of claim 7 wherein the thickness modulation is made in the form of a fractal structure.

11. The magneto-optical indicator element of claim 7 wherein the thickness modulation is made in the form of a self-affine structure.

12. A magneto-optical indicator element comprising:
a substrate; and
a thin film indicator structure comprising a plurality of thin-film layers disposed on a said substrate, at least one of said layers comprising magneto-optically (MO)-active material having predetermined magnetic properties including magnetic anisotropy, magnetization saturation value, coercive field value; and a magneto-optical effect value; said indicator structure including at least one of said layers having a thickness and/or refractive index modulated in a predetermined fashion; said indicator structure having at least one optical mode which is at least partially localized within and/or at at least one interface of said at least one MO-active layer; said at least one optical mode being at least partially localized in said one layer having modulated thickness and/or refractive index,
wherein the optical mode is a waveguide mode.

13. The magneto-optical indicator element of claim 12 wherein said waveguide mode is at least partially localized in the at least one MO-active layer.

14. The magneto-optical indicator element of claim 13 wherein the MO-active layer possesses a positive real part of the dielectric permittivity in the operational wavelength range of the magneto-optical indicator film.

15. The magneto-optical indicator element of claim 14 wherein the at least one layer with a modulated thickness is made of dielectric material that is transparent in the operational wavelength range of the magneto-optical indicator film.

16. The magneto-optical indicator element of claim 15 wherein the thickness modulation is made in the form of self-assembled, ordered colloids made of dielectric material that is transparent in the operational wavelength range of the magneto-optical indicator film.

17. The magneto-optical indicator element of claim 14 wherein the MO-active layer is selected from the group consisting of:
iron garnets modified with at least one element selected from the group consisting of Bi, Y, Ga, Ce;
iron garnets modified with at least one element selected from the group consisting of rare earth elements;
intermetallic compounds and alloys;
ferromagnetic oxides;
magnetic semiconductors.

18. The magneto-optical indicator element of claim 14 wherein the substrate is a monocrystalline substrate.

19. The magneto-optical indicator element of claim 18 wherein the MO-active layer is single crystal layer.

20. The magneto-optical indicator element of claim 19 wherein the MO-active layer possesses magnetic anisotropy chosen from the group consisting of:
in-plane easy-axis anisotropy, perpendicular anisotropy, easy-plane anisotropy.

21. A magneto-optical indicator element comprising:
a substrate; and
a thin film indicator structure comprising a plurality of thin-film layers disposed on a said substrate, at least one of said layers comprising magneto-optically (MO)-active material having predetermined magnetic properties including magnetic anisotropy, magnetization saturation value, coercive field value; and a magneto-optical effect value; said indicator structure including at least one of said layers having a thickness and/or refractive index modulated in a predetermined fashion; said indicator structure having at least one optical mode which is at least partially localized within and/or at at least one interface of said at least one MO-active layer; said at least one optical mode being at least partially localized in said one layer having modulated thickness and/or refractive index,
wherein the optical mode is a hybrid surface plasmon mode.

22. A method of manufacturing a magneto-optical indicator element comprising:
providing a substrate,
applying, onto said substrate, a thin film indicator structure comprising a plurality of thin-film layers, at least one of said layers comprising magneto-optically (MO)-active material having predetermined magnetic properties including magnetic anisotropy, magnetization saturation value, coercive field value; and a magneto-optical effect value, and
modulating the thickness and/or refractive index of at least one of said layers in a predetermined fashion so that said indicator structure exhibits at least one optical mode which is at least partially localized within and/or at at least one interface of said at least one MO-active layer; said at least one optical mode being at least partially localized in said one layer having modulated thickness and/or refractive index
wherein the optical mode is a hybrid surface plasmon mode.

23. An optical apparatus comprising:
a light source;
a light detector; and
a magneto-optical indicator element disposed along an optical path between said light source and said light detector, said magneto-optical indicator element comprising a substrate and a thin film indicator structure comprising a plurality of thin-film layers disposed on a said substrate, at least one of said layers comprising magneto-optically (MO)-active material having predetermined magnetic properties including magnetic anisotropy, magnetization saturation value, coercive field value; and
a magneto-optical effect value; said indicator structure including at least one of said layers having a thickness and/or refractive index modulated in a predetermined fashion;
said indicator structure having at least one optical mode which is at least partially localized within and/or at at least one interface of said at least one MO-active layer; said
at least one optical mode being at least partially localized in said one layer having modulated thickness and/or refractive index,
wherein the optical mode is a hybrid surface plasmon mode.

* * * * *